(12) United States Patent
Leatherwood-Maxwell

(10) Patent No.: US 7,988,654 B2
(45) Date of Patent: Aug. 2, 2011

(54) BRACE HOSIERY APPARATUS, ASSEMBLY AND METHOD OF USE

(76) Inventor: Nona Leatherwood-Maxwell, Yukon, OK (US)

( * ) Notice: Subject to any disclaimer, the term of this patent is extended or adjusted under 35 U.S.C. 154(b) by 84 days.

(21) Appl. No.: 11/481,714

(22) Filed: Jul. 6, 2006

(65) Prior Publication Data

US 2007/0021701 A1  Jan. 25, 2007

Related U.S. Application Data

(60) Provisional application No. 60/696,901, filed on Jul. 6, 2005.

(51) Int. Cl.
*A61F 5/00* (2006.01)
*A61F 5/37* (2006.01)

(52) U.S. Cl. ............... 602/23; 602/27; 602/28; 602/29; 128/882

(58) Field of Classification Search ............ 602/16, 602/6, 26, 12, 5, 60, 61, 65, 3, 27–29; 128/856, 128/882; 2/22–23, 239–242
See application file for complete search history.

(56) References Cited

U.S. PATENT DOCUMENTS

| | | | | | |
|---|---|---|---|---|---|
| 1,287,870 | A | * | 12/1918 | Burk | 602/60 |
| 3,916,886 | A | * | 11/1975 | Rogers | 602/28 |
| 4,166,460 | A | * | 9/1979 | Applegate | 602/27 |
| 5,742,945 | A | * | 4/1998 | Lindaman | 2/239 |
| 6,146,344 | A | * | 11/2000 | Bader | 602/6 |
| 6,393,622 | B1 | * | 5/2002 | Rice | 2/406 |
| 7,314,457 | B2 | * | 1/2008 | Reaux | 602/6 |
| 2002/0026134 | A1 | * | 2/2002 | Dalton et al. | 602/3 |

* cited by examiner

*Primary Examiner* — Patricia M Bianco
*Assistant Examiner* — Ophelia Hawthorne
(74) *Attorney, Agent, or Firm* — Dunlap Codding, P.C.

(57) ABSTRACT

A brace hosiery apparatus including a hollow, cylindrical brace covering disposed about at least a portion of an orthotic brace and a first connector that when removably connected to a second connector secures the brace covering to the orthotic brace.

5 Claims, 3 Drawing Sheets

BRACE HOSIERY APPARATUS, ASSEMBLY AND METHOD OF USE

CROSS-REFERENCE TO RELATED APPLICATIONS

The present application claims priority to the provisional patent application identified by the U.S. Ser. No. 60/696,901, which was filed on Jul. 6, 2005, the entire content of which is hereby expressly incorporated by reference in its entirety.

FIELD OF EMBODIMENTS

The exemplary embodiments detailed relate generally to the field of brace hosiery apparatus, orthotic hosiery assemblies and methods using brace hosiery apparatus and orthotic hosiery assemblies.

BACKGROUND

Orthotic braces are commonly used to adjust irregularities in the foot, ankle, or leg and to diminish pain and discomfort in the feet, legs, hips, back and neck. While the use of orthotic braces can be beneficial to the user, orthotic braces tend to rub against the user's skin which can cause chafing, blistering, pain and sweating. Also, orthotic braces are not generally considered to be visually appealing which tends to draw unwanted attention to the user.

To this end, a need exists for an apparatus that can prevent the orthotic brace from rubbing against the user's skin and provide a cushioned barrier while camouflaging the brace and granting the user a more visually appealing orthotic system. It is to such an apparatus that the exemplary embodiments shown and described herein are directed.

DETAILED DESCRIPTION OF EXEMPLARY EMBODIMENTS

The following detailed description and the appended drawings describe and illustrate exemplary embodiments for the purpose of enabling one of ordinary skill in the relevant art to make and use a brace hosiery apparatus and an orthotic hosiery assembly. The description and drawings are not intended to limit scope or protection, in any manner.

Figure 1:
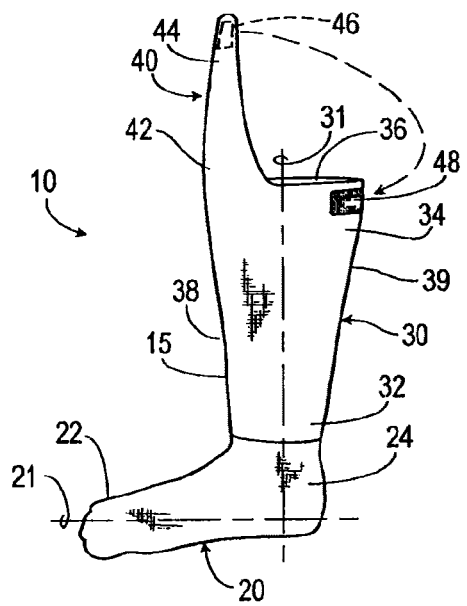
FIG. 1 is a perspective view of a brace hosiery apparatus comprising an extension and a brace covering having an upper section and a lower section.

FIG. 1 illustrates an exemplary embodiment of a brace hosiery apparatus 10. The brace hosiery apparatus 10 is used in connection with an orthotic device, such as a brace 100 shown in FIG. 2. The brace hosiery apparatus 10 includes a brace covering 15 having a lower section 20 and an upper section 30 and an extension 40. The brace covering 15 is constructed to be disposed about at least a portion of the orthotic brace 100 and to be secured to the brace by way of the extension 40.

The lower section 20 of the brace covering 15 is a flexible, hollow, cylindrical structure with a longitudinal axis 21 extending between a first end 22 and a second end 24. The lower section 20 may be fabricated of conforming material having characteristics of absorbency, elasticity, comfort and durability and can be natural or synthetic material, cloth or cloth-like material such as, by the way of example but not limitation, cotton, polyester, rayon, nylon, spandex, elastic, rubber, wool, polymers or combinations and derivations thereof. The material includes basic hosiery colors that include, but are not limited to, white, black, beige, blue and brown. The material may also contain patterns, textures, designs or combinations thereof.

The upper section 30 of the brace covering 15 is a hollow, flexible, cylindrical structure with a longitudinal axis 31 extending between a first end 32 and a second end 34. The first end 32 of the upper section 30 is integrated with the lower section 20 of the brace covering 15 or connected to the lower section 20 of the brace covering 15 at the second end 24 of the lower section 20. The longitudinal axis 21 of the lower section 20 and the longitudinal axis 31 of the upper section 30 are substantially perpendicular.

The second end 34 of the upper section 30 defines an opening 36. The upper section 30 also has an anterior side 38 and a posterior side 39. The material, colors, patterns, textures and designs of the upper section 30 may be similar but are not restricted to the material colors, patterns, textures and designs of the lower section 20.

The extension 40 of the brace hosiery apparatus 10 has a proximal end 42 and a distal end 44. The proximal end 42 of the extension 40 is integrated with the second end 34 of the upper section 30 of the brace covering 15 or connected to the second end of the upper section 30 of the brace covering 15. As illustrated in FIG. 1, the extension 40 is integrated with the second end 34 of the upper section 30 on the anterior side 38 of the upper section 30. However, the extension 40 may be connected at any point along the second end 34 of the upper section 30. The material, colors, patterns, textures and designs of the extension 40 may be similar but are not restricted to the material colors, patterns, textures and designs of the lower section 20 and/or upper section 30.

The distal end 44 of the extension 40 includes a first connector 46 integrated or connected to the distal end 44 of the extension 40. The first connector 46 is removably connectable to a second connector 48. The second connector 48 is integrated with or connected to the second end 34 of the upper section 30 of brace hosiery apparatus 10. The second connector 48 is located on the posterior side 39 of the second end 34 of the upper section 30. The first connector 46 contacts the second connector 48 when the extension 40 is folded over the opening 36 of the brace covering 15.

In another embodiment, the first connector 46 is located on the interior of the brace covering 15 on the anterior side 38 of the upper section 30. The second connector 48 is located on the posterior side of the upper section on the exterior of the brace covering 15. The first connector 46 contacts the second connector 48 when the anterior side 38 the upper section 30 of the brace covering 15 is extended over the opening 36.

The first connector 46 and secondary connector 48 may be removably connectable by such means as ribbons, hook-and-loop material, elastic material, snaps, button and button hole, combinations and derivations thereof or any other means for selectively removably connecting the first connector 46 to the secondary connector 48.

Figure 2:
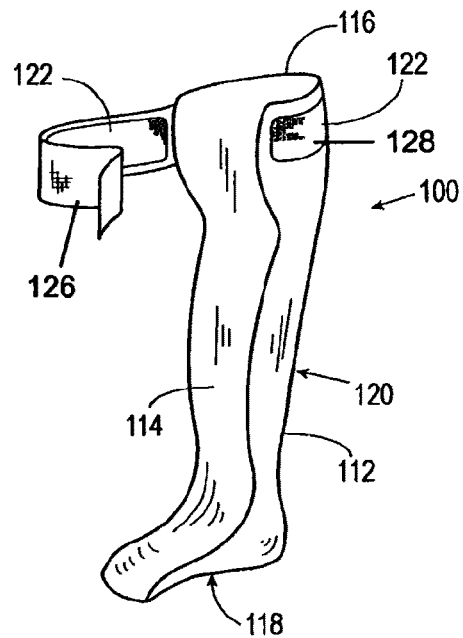
FIG. 2 is a perspective view of a brace.

FIG. 2 illustrates the brace 100 having an exterior surface 112, an interior surface 114 and a rim 116. Typically a brace includes a sole 118, a body 120 and a securing assembly 122. The sole 118 of the brace 100 extends substantially perpendicular from a lower section of the body 120. The upper section of the body 120 has the rim 116. The sole 118 and body 120 of the brace 100 are made of a light weight polymer and shaped to substantially conform to a foot or ankle for stabilizing, supporting and bracing the user's foot, ankle and/or leg.

The securing assembly 122 of the brace 100 is for securing the sole 118 and/or body 120 of the brace to the foot, ankle and/or leg of the user, while allowing the brace to be selectively removable from the foot, ankle and/or leg. In FIG. 2, the securing assembly 122 secures the leg portion to the leg of an individual with the sole 118 positioned over a portion of the bottom of the individual's foot. The securing assembly 122 may include a first connection member 126 extending from the leg portion 120 and Being extendable over the invidual's leg and a second connection member 128 Positioned on the exterior side of the leg portion 120. One example of such brace 100 is the Drop Foot Brace, fabricated in a predorsiflexed position, designed to fit into a standard shoe, sandal or boot and commercially available from MedMarketPlace Direct located at 1541 East Commercial Boulevard, in Fort Lauderdale, Fla. 3334. However, the brace 100 may be any type of brace typically utilized to stabilize, brace and/or support the user's foot, ankle and/or leg. Foot, ankle, leg and neck braces are known in the art and therefore no further description of the brace is deemed necessary.

Figure 3A:
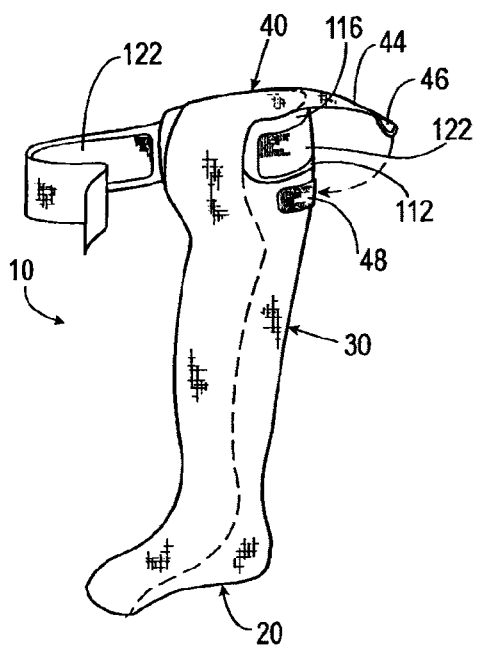
FIGS. 3A and 3B are perspective views of an orthotic hosiery assembly.
Figure 3B:
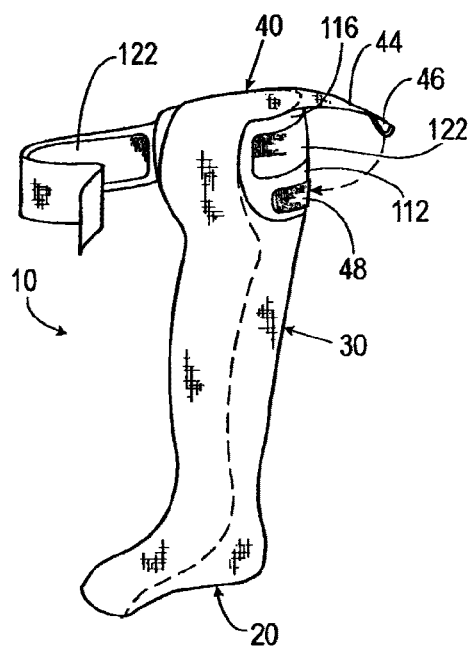

Referring now to FIGS. 3A and 3B, the brace hosiery apparatus 10 is shown in use with the brace 100. The brace covering 15 is disposed about the brace 100 so as to substantially cover the sole 118 and the body 120 with the lower section 20 covering the sole 118 and the upper section 30 covering the body 120 of the brace 100. The conforming material of the brace covering 15 substantially conforms to the contour of the brace 100 upon the user securing the brace 100 to the user's body.

The extension 40 of the brace hosiery apparatus 10 extends up the interior surface 114 of the brace 100 to the rim 116 of the brace. The extension 40 folds over the rim 116 of the brace 100 allowing the first connector 46 on the distal end 44 of the extension 40 to contact the second connector 48, thereby securing the brace covering 15 to the brace 100. The first connector 46 is removably connected to the second connector 48.

In FIG. 3A, the second connector 48 is located on the upper section 30 of the brace covering 15. However, as shown in FIG. 3B, the second connector 48 may be located on the exterior surface 112 of the brace 100.

Figure 4:
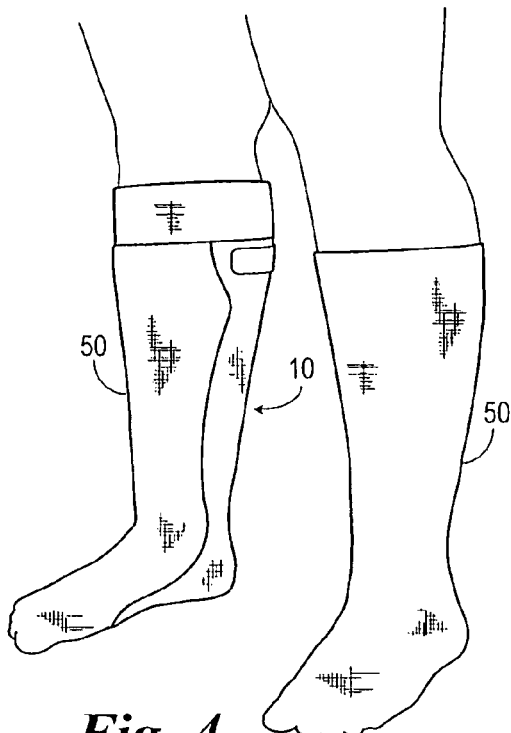
FIG. 4 is a perspective view of an orthotic hosiery assembly in use with a sock.

Referring to FIG. 4, a user will place a sock 50 similar in appearance to the brace hosiery apparatus 10 on the user's foot. With the brace hosiery apparatus 10 secured to the brace 100, the user secures the brace 100 to the user's leg via the securing assembly 122 of the brace 100.

The material of the lower section 20 and the upper section 30 of the brace covering 15 may be designed to substantially match the visual appearance of the sock 50 worn by the user such that the sock 50 and the conforming material visually blend together camouflaging the brace 100. In camouflaging, the brace covering 15 will substantially match at least one color, pattern, design, texture, or other characteristic with at least one color, pattern, design, texture, or other characteristic of the user's sock 50. The brace hosiery apparatus 10 can be designed to be used in conjunction with a multitude of sock options including, by the way of example, but not limitation, knee socks, anklets, crew socks, tube socks, dress trouser socks and hosiery products.

The material of the brace covering 15 may also be flesh-toned and create the appearance the user is not wearing the brace 100. With the flesh-toned appearance, the user has the option of not wearing a sock.

Another embodiment may include an orthotic hosiery kit. The orthotic hosiery kit includes the brace hosiery apparatus 10 and the sock 50 designed and manufactured to match in visual appearance to the brace hosiery apparatus. The sock 50 may provide further support for the user's foot, ankle and/or leg, or the sock 50 may be used solely for covering and protecting the user's foot.

Figure 5:
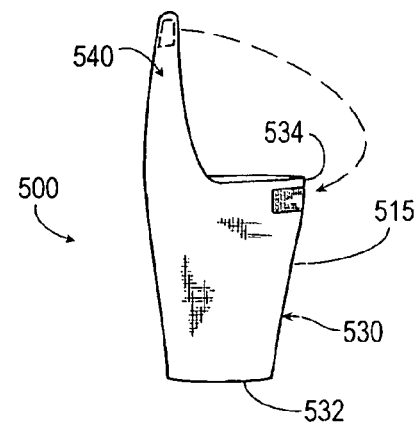
FIG. 5 is a perspective view of a brace hosiery apparatus comprising an extension and a brace covering having an upper section.

FIG. 5 illustrates another embodiment of a brace hosiery apparatus 500. In this embodiment, the brace hosiery apparatus 500 includes an extension 540 and a brace covering 515 having an upper section 530. The upper section 530 is a flexible, hollow structure having first end 532 and a second end 534, both being open ends.

Figure 6:
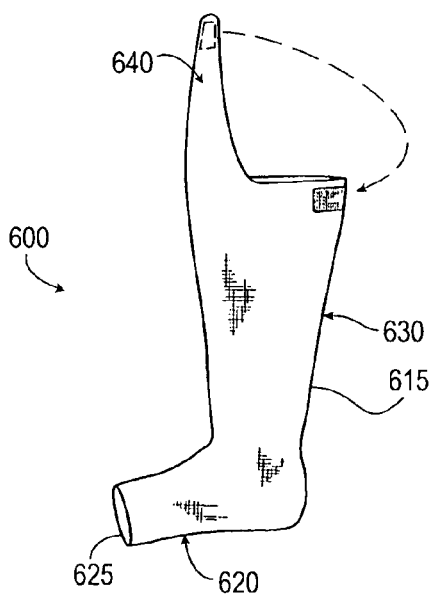
FIG. 6 is a perspective view of a brace hosiery apparatus comprising an extension and a brace covering having an upper section and a lower section with an open end.

FIG. 6 illustrates another embodiment of a brace hosiery apparatus 600. In this embodiment, the brace hosiery apparatus 600 includes a brace covering 615 having a lower section 620 and an upper section 630 and an extension 640. The lower section 620 has a first end 625. The first end 625 of the lower section 620 is open so that the toes of the user's foot are not enclosed within the brace covering 615.

Figure 7:
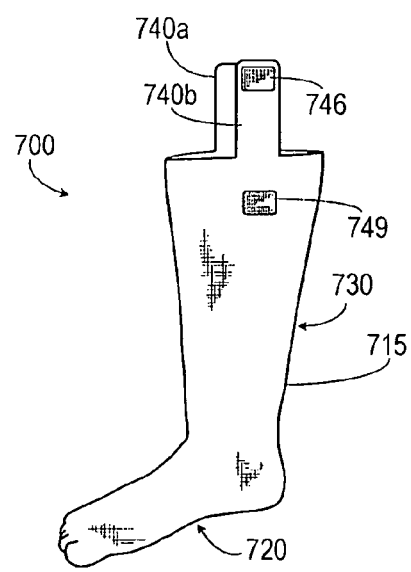
FIG. 7 is a perspective view of a brace hosiery apparatus comprising multiple extensions and a brace covering having an upper section and a lower section.

FIG. 7 illustrates another embodiment of a brace hosiery apparatus 700. In this embodiment, the brace hosiery apparatus 700 includes a brace covering 715 having a lower section 720 and an upper section 730, a first extension 740a and a second extension 740b. Each extension 740a and 740b has a first connector 746 for attachment to a second connector 749 disposed on the brace covering 715 or on the brace 100.

Figure 8:
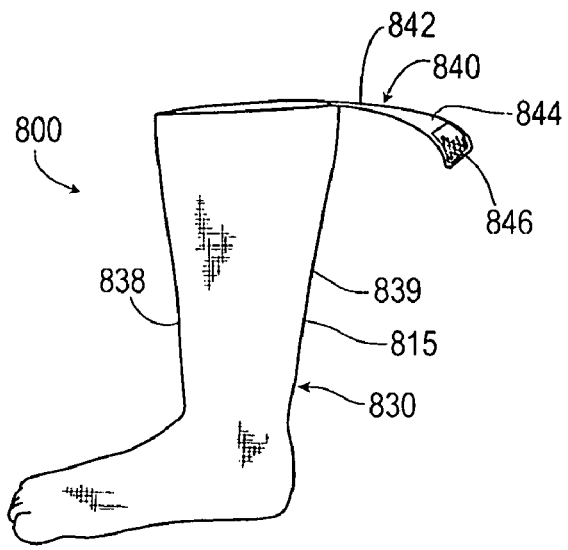
FIG. 8 is a perspective view of a brace hosiery apparatus comprising an extension and a brace covering having an upper section and a lower section.

FIG. 8 illustrates another embodiment of a brace hosiery apparatus 800. In this embodiment, the brace hosiery apparatus 800 includes a brace covering 815 having an upper section 830 and an extension 840. The upper section 830 has an anterior side 838 and a posterior side 839. Connected to the posterior side 839 of the upper section 830, the extension 840 has a proximal end 842 and a distal end 844. The distal end 844 of the extension is integrated or connected to a first connector 846. The first connector 846 is removably connected to a second connector (not shown) located on the exterior surface 112 of the brace 100.

Figure 9:
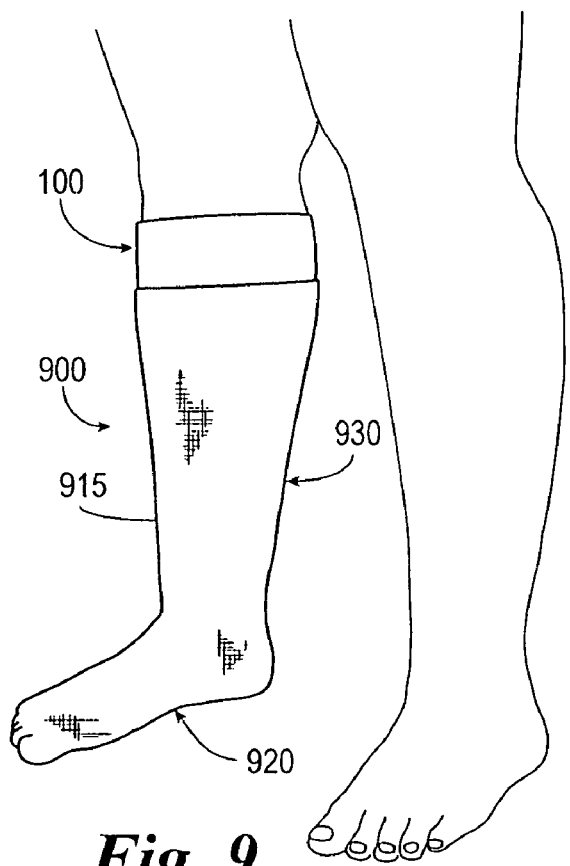
FIG. 9 is a perspective view of an orthotic hosiery assembly wherein the brace hosiery apparatus covers the brace and the user's foot.

FIG. 9 illustrates another embodiment of a brace hosiery apparatus 900. In this embodiment, the brace hosiery apparatus 900 is designed and configured to fit a brace covering 915 having a lower section 920 and an upper section 930 over the brace 100 and also the user's foot.

The embodiments shown in the drawings and described above are exemplary of numerous embodiments that may be made within the scope of the appended claims. It is contemplated that numerous other configurations of the brace covering, extension, as well as the first connector and the second connector may be used with varying braces 100. In addition, the material of each component may be selected from numerous materials other than those specifically disclosed. In short, it is the applicant's intention that the scope of the patent issuing will be limited only by the scope of the appended claims.

What is claimed is:

1. An orthotic brace assembly, comprising: an orthotic brace having an interior surface, an exterior surface, a sole portion shaped to conform to at least a portion of an individual's foot, and a leg portion extending from the sole portion and shaped to conform to at least a portion of the individual's leg, the leg portion having a rim at an upper end thereof, the brace further including means for adjustably securing the sole portion and the leg portion to the individual's foot and leg; and a brace hosiery apparatus including a brace covering having an anterior side and a posterior side, the brace covering disposed about the sole portion and the leg portion of the brace so that the anterior side substantially covers the interior surface of the brace and the posterior side substantially covers the exterior surface of the brace, the brace covering being fabricated of an elastic material such that the brace covering conforms to the contour of the interior surface and the exterior surface of the brace upon the sole portion and the leg portion of the brace being positioned on an individual's foot and leg, the brace hosiery apparatus further having an extension of said brace hosiery extending away from an upper end of the anterior side of the brace covering, the extension extending over the rim of the leg portion and including a connector mechanism to allow for detachably connecting to one of the exterior side of the brace and the posterior side of the brace covering so as to secure the brace covering to the brace.

2. The orthotic brace assembly of claim 1, wherein the means for adjustably securing the brace comprises:
    a first connecting member extending from the leg portion and being extendable over the individual's leg; and
    a second connecting member positioned on the exterior side of the leg portion,
    wherein the brace covering is configured such that the second connecting member is exposed with the brace covering disposed about the leg portion of the orthotic brace so as to permit the first connecting member to be selectively attached to the second connecting member.

3. The orthotic brace assembly of claim 1, wherein the connector mechanism comprises: a first connector located on a distal end of the extension of the brace covering; and a second connector located on the exterior surface of the leg portion of the orthotic brace.

4. The orthotic brace assembly of claim 1, wherein the connector mechanism comprises: a first connector located on a distal end of the extension; and a second connector located on the posterior side of the brace covering.

5. The orthotic brace assembly of claim 1, wherein the brace covering has a closed lower end.

* * * * *

UNITED STATES PATENT AND TRADEMARK OFFICE
CERTIFICATE OF CORRECTION

| | | |
|---|---|---|
| PATENT NO. | : 7,988,654 B2 | Page 1 of 1 |
| APPLICATION NO. | : 11/481714 | |
| DATED | : August 2, 2011 | |
| INVENTOR(S) | : Nona Leatherwood-Maxwell | |

It is certified that error appears in the above-identified patent and that said Letters Patent is hereby corrected as shown below:

In the Specification:

Column 3, line 30: Delete "Being" and replace with -- being --
Column 3, line 30: Delete "invidual's" and replace with -- individual's --
Column 3, line 31: Delete "connection" and replace with -- connecting --
Column 3, line 31: Delete "Positioned" and replace with -- positioned --

Signed and Sealed this
Thirty-first Day of January, 2012

David J. Kappos
*Director of the United States Patent and Trademark Office*